US011141677B2

(12) United States Patent
Augier et al.

(10) Patent No.: US 11,141,677 B2
(45) Date of Patent: Oct. 12, 2021

(54) METHOD FOR SELECTIVELY SEPARATING IMPURITIES PRESENT IN A HYDRO-ALCOHOLIC CUT BY RECYCLING THROUGH A LIQUID-LIQUID EXTRACTION COLUMN

(71) Applicants: IFP Energies nouvelles, Rueil-Malmaison (FR); COMPAGNIE GENERALE DES ETABLISSEMENTS MICHELIN, Clermont-Ferrand (FR)

(72) Inventors: Frederic Augier, Rueil-Malmaison (FR); Damien Leinekugel Le Cocq, Rueil-Malmaison (FR); Rejane Dastillung, Rueil-Malmaison (FR); Pierre Balz, Rueil-Malmaison (FR)

(73) Assignees: IFP Energies nouvelles, Rueil-Malmaison (FR); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 0 days.

(21) Appl. No.: 16/971,498

(22) PCT Filed: Jan. 25, 2019

(86) PCT No.: PCT/FR2019/050170
§ 371 (c)(1),
(2) Date: Aug. 20, 2020

(87) PCT Pub. No.: WO2019/162586
PCT Pub. Date: Aug. 29, 2019

(65) Prior Publication Data
US 2020/0398181 A1 Dec. 24, 2020

(30) Foreign Application Priority Data
Feb. 22, 2018 (FR) ...................................... 1851549

(51) Int. Cl.
*C07C 29/84* (2006.01)
*C07C 45/83* (2006.01)
*B01D 3/14* (2006.01)
*B01D 11/04* (2006.01)
*C07C 31/08* (2006.01)
*C07C 47/06* (2006.01)

(52) U.S. Cl.
CPC ............ *B01D 3/14* (2013.01); *B01D 11/0426* (2013.01); *B01D 11/0488* (2013.01); *C07C 29/84* (2013.01); *C07C 45/83* (2013.01); *C07C 31/08* (2013.01); *C07C 47/06* (2013.01)

(58) Field of Classification Search
CPC .......... C07C 29/83; C07C 29/84; C07C 45/83
See application file for complete search history.

(56) References Cited

U.S. PATENT DOCUMENTS

| 2,393,381 | A | 1/1946 | Kinsey et al. |
| 2,395,057 | A | 2/1946 | Marsh et al. |
| 2,403,742 | A | 7/1946 | Murray et al. |
| 2,403,743 | A | 7/1946 | Hitcheock et al. |
| 2,439,587 | A | 4/1948 | Stahly |
| 9,950,969 | B2 | 4/2018 | Dastillung et al. |
| 10,358,396 | B2 | 7/2019 | Dastillung et al. |
| 10,654,763 | B2 | 5/2020 | Dastillung et al. |

FOREIGN PATENT DOCUMENTS

| FR | 3026100 A1 | 3/2016 |
| FR | 3026101 A1 | 3/2016 |
| WO | 18001982 A1 | 1/2018 |

OTHER PUBLICATIONS

International Search Report PCT/FR2019/050170 dated Mar. 27, 2019 (pp. 1-2).

*Primary Examiner* — Sikarl A Witherspoon
(74) *Attorney, Agent, or Firm* — Millen White Zelano & Branigan

(57) ABSTRACT

Liquid-liquid extraction and distillation of a liquid feedstock of at least ethanol, water, acetaldehyde and at least one hydrocarbon-based impurity with a boiling point of between 20° C. and 100° C. at atmospheric pressure, or which generates, with at least one of the compounds of the liquid feedstock and/or with the organic extraction solvent and/or with the aqueous back-washing solvent, an azeotrope and a partition coefficient of between 0.1 and 5 at any point in a back-washing (BW) column of the extraction section, by (a) a liquid-liquid extraction step a washing (W) column, a back-washing (BW) column and at least one injection (F2) of a cut withdrawn in step b), located in the top half of the back-washing column, (b) distillation of an aldehyde and ethanol separation producing at least one aldehyde-rich effluent, one ethanol-rich effluent and one water-rich effluent.

9 Claims, 3 Drawing Sheets

METHOD FOR SELECTIVELY SEPARATING IMPURITIES PRESENT IN A HYDRO-ALCOHOLIC CUT BY RECYCLING THROUGH A LIQUID-LIQUID EXTRACTION COLUMN

CONTEXT OF THE INVENTION AND PRIOR ART

Processes for producing butadiene from ethanol were developed in particular by Russian teams on the basis of the studies by Lebedev in the 1920s and by American teams during the Second World War starting with the studies by Ostromilenski.

In these processes, the conversion per pass ranges between about 30% and 60%, which implies considerable recycling of the ethanol and acetaldehyde. Furthermore, a wide variety of impurities of different nature (saturated, unsaturated or aromatic hydrocarbons, oxygen-based products such as alcohols, ketones, aldehydes, phenols, acids, esters, ethers) and having very different molar masses is produced (between 50 and 10 000 g/mol).

Consequently, it is thus necessary to establish a sequence of unit operations for the purpose of removing a maximum amount of impurities while losing as little ethanol and acetaldehyde as possible so as to increase the yield to the limits of the process, to avoid accumulating these impurities in the process and to avoid their reactivity with feed equivalents, or even poisoning of the catalysts. From an economic viewpoint, it is essential to reduce the production cost of butadiene, which requires:

- losing as little ethanol and acetaldehyde as possible,
- not recycling impurities in the reactors, which impurities would result in a fall in selectivity toward butadiene or would accumulate to unacceptable levels, requiring a purge and thus losses of ethanol and acetaldehyde.

At the outlet of the catalytic reactors, the effluent produced, composed of butadiene, acetaldehyde, water, ethanol and impurities, undergoes several unit operations in order to separate the most volatile byproducts from the less volatile byproducts.

Among the most volatile byproducts, mention may be made of hydrogen, carbon monoxide, carbon dioxide, and $C_1$-$C_4$ alkanes and olefins. It is essential to remove these byproducts from the butadiene-rich effluent in order to obtain a product within the specifications.

Among the less volatile byproducts, mention may be made of acetone, diethyl ether, butanol, butanal, butenol, butanone, ethyl acetate, crotonaldehyde, acetic acid, methanol and other apolar impurities. Other byproducts are generated in a smaller amount in the reaction zone. In the continuation of the document, the term "impurities" will denote this combination of hydrocarbon-based or oxygen-based compounds.

In the first process schemes of the American teams, ethanol, acetaldehyde, water and the liquid byproducts were separated by a line of three distillation columns (U.S. Pat. No. 2,403,742). The effluent rich in ethanol, acetaldehyde, water and liquid byproducts feeds a first distillation column in which an acetaldehyde-rich effluent is separated from the remainder of the effluent. A second distillation column makes it possible to separate the liquid byproducts from an effluent rich in ethanol and water. The final distillation column makes it possible to separate the ethanol from the water. Most of the process patents filed in the period 1940-1960 by the companies Carbide & Carbon and Koppers (U.S. Pat. Nos. 2,403,743, 2,393,381, 2,395,057 and 2,439,587) are directed toward improving this part of the scheme. However, the separation is not total and impurities are found in the ethanol-rich effluent, with which they are recycled into the catalytic reactors.

In patent applications FR 3 026 100 (A1) and FR 3 026 101 (A1), the liquid impurities are removed by liquid-liquid extraction. The effluent composed of ethanol, acetaldehyde, water and impurities feeds a liquid-liquid extraction section composed of a column (W) for washing the effluent with an organic solvent and a column (BW) for back-washing with water. The washing (W) column is fed at the bottom with the washing solvent, the aim of which is to wash the feedstock counter-currentwise. The washing solvent used for this unit operation may contain saturated and/or unsaturated and/or aromatic hydrocarbons, advantageously consisting of a mixture of hydrocarbons containing between 6 and 40 carbon atoms. It may be a desulfurized gas oil or kerosene cut or alternatively a hydrocarbon cut produced by a unit of Fischer-Tropsch type. The organic solvent used is then regenerated by distillation and reused. At the outlet of the washing (W) column, the extract is predominantly composed of the washing solvent, of extracted byproducts and of a small amount of ethanol and acetaldehyde. This extract is subsequently washed with water in the back-washing (BW) column with the aim of re-extracting the ethanol and the acetaldehyde and thus minimizing the losses of ethanol and acetaldehyde.

In patent applications FR 3 026 100 (A1) and FR 3 026 101 (A1), liquid-liquid extraction enables the removal of a large proportion of the impurities, notably of the apolar and sparingly polar impurities, and of the brown oils. However, certain hydrocarbon-based impurities, in particular partially polar hydrocarbon-based impurities, for instance butanol, are very sparingly extracted during this liquid-liquid extraction. The raffinate leaving at the bottom of the extraction section thus still contains, besides ethanol, acetaldehyde and water, many impurities, for instance butanol or indeed methanol, and ethyl acetate.

Furthermore, in patent applications FR 3 026 100 (A1) and FR 3 026 101 (A1), the raffinate leaving at the bottom of the extraction section is then sent to a distillation section, with 2 or 3 columns, the purpose of which is to separate the ethanol, acetaldehyde and water compounds, the latter concentrating a large portion of the impurities that are still present. The impurities, having a boiling point between those of the reagents, ethanol and acetaldehyde, and that of water, i.e. between about 20° C. and about 100° C., may potentially accumulate in one or other of the distillation columns. This accumulation may bring about several phenomena that are undesired or even harmful toward the correct functioning of the distillation columns. It may notably bring about local demixing (creation of a second liquid phase) which reduces the separation efficiency, or modification of the thermodynamic equilibria between the species present in the accumulation zone. For example, the butanol present in the raffinate at the liquid-liquid extraction outlet, and given that butanol forms an azeotrope with water with a boiling point of about 92° C., has a tendency to accumulate in the ethanol/water distillation column.

A simple solution to this problem would consist in performing continuous or batch withdrawal in the distillation column so as to purge the impurity under consideration. However, this withdrawal would contain the impurity diluted in the compounds of interest, notably ethanol and acetaldehyde. It might thus represent a loss of "noble" species, of industrial interest.

One object of the invention is to improve the separation of the hydrocarbon-based impurities, in particular of the partially polar hydrocarbon-based impurities, which are byproducts of the catalytic reaction for the transformation of ethanol into butadiene, while at the same time optimizing the recovery of the ethanol and acetaldehyde. The advantage of the invention lies in the fact that this optimization is envisaged without multiplying the effluent treatment steps. The invention advantageously applies, in particular, to the ethanol/acetaldehyde/water effluent in the processes of patent applications FR 3 026 100 (A1) and FR 3 026 101 (A1).

SUMMARY OF THE INVENTION

The present invention relates to a process for the treatment by liquid-liquid extraction and distillation of a liquid feedstock comprising at least ethanol, water and acetaldehyde and at least one hydrocarbon-based impurity with a boiling point of between 20 and 100° C. at atmospheric pressure, or generating, with at least one of the compounds of the liquid feedstock and/or with the organic extraction solvent and/or with the aqueous back-washing solvent, an azeotrope whose boiling point is between 20 and 100° C. at atmospheric pressure, and a partition coefficient of between 0.1 and 5 at any point in the back-washing (BW) column of the extraction section, comprising:
  a) a liquid-liquid extraction step comprising an extraction section comprising a washing (W) column and a back-washing (BW) column, said extraction section being fed with said liquid feedstock at an intermediate point located between the top of the washing (W) column and the bottom of the back-washing (BW) column,
    said washing (W) column being fed at the top with the stream originating from the bottom of the back-washing (BW) column and at the bottom with a stream of an organic extraction solvent,
    said back-washing (BW) column being fed at the top with a stream of an aqueous back-washing solvent and at the bottom with the stream originating from the top of the washing (W) column,
    said extraction section comprising at least one injection (F2) of the cut withdrawn in step b), said injection (F2) being located in the top half of the back-washing (BW) column,
    said extraction section producing, at the bottom of the washing (W) column, a raffinate comprising at least water, ethanol, acetaldehyde and a portion of said hydrocarbon-based impurity and, at the top of the back-washing (BW) column, an extraction effluent comprising at least a portion of said hydrocarbon-based impurity;
  b) a distillation step comprising:
    at least one acetaldehyde separation step comprising an acetaldehyde separation section, composed of at least one distillation column (D1) fed with the raffinate originating from step a) in an intermediate zone of the column (D1) and producing at the top an acetaldehyde-rich effluent and at the bottom a water/ethanol effluent; and
    at least one ethanol separation step comprising an ethanol separation section, composed of at least one distillation column (D2) fed with the water/ethanol effluent originating from the bottom of the column (D1) in an intermediate zone of the column (D2), and producing at the top an ethanol-rich effluent and at the bottom a water-rich effluent,
    at least one side withdrawal on the column (D1) or the column (D2) of a cut comprising at least one of the compounds ethanol or acetaldehyde, at a mass fraction of at least 10% of the total mass of the withdrawn cut, and said hydrocarbon-based impurity, at a mass fraction of between 0.5% and 50% of the total mass of the withdrawn cut, the side withdrawal being located in an intermediate zone of the column (D1) or (D2).

The process according to the invention consists in partially extracting from the feedstock a hydrocarbon-based impurity that is difficult to separate out, by conventional extraction-distillation, in a single pass, said hydrocarbon-based impurity, preferably at a low content in the feedstock to be treated, having an intermediate boiling point, or forming, with at least one of the compounds of the liquid feedstock, notably with water, ethanol and/or acetaldehyde, in particular with water, and/or with the organic extraction solvent and/or the aqueous back-washing solvent of step a) of the process according to the invention, an azeotrope with an intermediate boiling point, relative to the boiling points of the compounds of interest of the feedstock (ethanol, acetaldehyde and water), and having low affinity for the extraction solvent.

It has thus been discovered, surprisingly, that it is possible to at least partially extract this hydrocarbon-based impurity, in particular partially polar impurity, which is difficult to separate out, by means of a system for withdrawing and recycling a cut containing said hydrocarbon-based impurity, into the back-washing column. The inventors have in point of fact demonstrated that, when the hydrocarbon-based impurity has affinity for the extraction solvent that is low but higher than that for ethanol and that for acetaldehyde, the fact of reinjecting the withdrawn cut containing the hydrocarbon-based impurity that is difficult to separate out in the top part of the back-washing column makes it possible to extract at least a fraction of the reinjected hydrocarbon-based impurity, without significant loss of ethanol and acetaldehyde, and for a moderate cost.

Advantageously, the process according to the invention makes it possible to produce an effluent that is concentrated in acetaldehyde and an effluent that is concentrated in ethanol, without significant loss of these compounds, and while at the same time limiting the energy consumption.

The invention advantageously applies to the treatment of the aqueous-alcoholic effluents obtained from the conversion of ethanol into butadiene. In particular, the process according to the invention advantageously applies to the step of removing the hydrocarbon-based impurities and the brown oils, which is described, for example, in patent applications FR 3 026 100 (A1) and FR 3 026 101 (A1), this removal step comprising, inter alia, a liquid-liquid extraction section and a distillation section.

The effluents produced according to the invention, in particular the effluent concentrated in acetaldehyde and the effluent concentrated in ethanol, can be recycled as reagents into the process for converting ethanol into butadiene, known as the Lebedev process, to produce butadiene and thus to improve the overall butadiene production yield.

DESCRIPTION OF THE INVENTION

According to the invention, the term "partition coefficient" (M) of a species i at a point in the extractor, means the ratio between the mass fraction of the species i under consideration in the organic extraction phase (Yi) and the mass fraction of this same species i in the aqueous phase (Xi). The organic extraction phase comprises the organic extraction solvent into which are notably extracted the apolar or sparingly polar impurities and at least partly the partially polar hydrocarbon-based impurity under consideration. The partition coefficient may vary substantially along the extractor. According to the invention, the term "extractor" means all of the washing (W) and back-washing (BW) columns in which the streams of organic phase and of aqueous phase circulate counter-currentwise. The partition coefficient under consideration according to the invention for assessing the hydrocarbon-based impurity extracted by means of the process according to the invention is the partition coefficient of this hydrocarbon-based impurity at any point in the back-washing (BW) column of the extraction section of step a) of the process according to the invention.

According to the invention, the term "partially polar hydrocarbon-based impurity" or "hydrocarbon-based impurity" means a hydrocarbon-based compound, other than ethanol and acetaldehyde, which is preferably present in small amounts in the liquid feedstock (notably in a content of less than or equal to 5% by weight of the feedstock to be treated), and which has affinity for the organic extraction phase comprising the organic extraction solvent which is low but better than those of ethanol and acetaldehyde, at any point in the back-washing (BW) column of the extraction section of the process according to the invention. The partition coefficient of the hydrocarbon-based impurity under consideration at any point in the back-washing (BW) column of the extraction section is also, advantageously, less than a value beyond which the hydrocarbon-based impurity may be considered as being apolar or sparingly polar and thus extracted with the organic extraction solvent during its first passage through the washing (W) column. This apolar or sparingly polar impurity should therefore not be present in the raffinate at the bottom of the washing (W) column. Thus, the invention is pertinent for extracting, at least partially, hydrocarbon-based impurities which have a partition coefficient of between 0.1 and 5 at any point in the back-washing (BW) column of the extraction section of step a) of the process according to the invention.

According to the present invention, the expression "between . . . and . . . " means that the limit values of the interval are included in the described range of values. If such were not the case and if the limit values were not included in the described range, such an clarification will be given by the present invention.

Thus, the present invention consists of a process for treating, by liquid-liquid extraction and distillation, a liquid feedstock comprising at least ethanol, water and acetaldehyde and at least one hydrocarbon-based impurity with a boiling point of between 20° C. and 100° C. at atmospheric pressure, or which generates, with at least one of the compounds of the liquid feedstock and/or with the organic extraction solvent and/or with the aqueous back-washing solvent, an azeotrope whose boiling point is between 20 and 100° C. at atmospheric pressure, and a partition coefficient of between 0.1 and 5 at any point in the back-washing (BW) column of the extraction section, comprising:
  a) a liquid-liquid extraction step comprising an extraction section comprising a washing (W) column and a back-washing (BW) column, said extraction section being fed with said liquid feedstock at an intermediate point located between the top of the washing (W) column and the bottom of the back-washing (BW) column,
  said washing (W) column being fed at the top with the stream originating from the bottom of the back-washing (BW) column and at the bottom with a stream of an organic extraction solvent, preferably at a mass flow rate of between 25% and 200% of the mass flow rate of the stream for feeding said liquid feedstock,
  said back-washing (BW) column being fed at the top with a stream of an aqueous solvent, preferably at a mass flow rate of between 10% and 80% of the mass flow rate of the stream for feeding said liquid feedstock, and at the bottom with the stream originating from the top of the washing (W) column,
  said extraction section comprising at least one injection (F2) of the cut withdrawn in step b), preferably at a mass flow rate of between 0.1% and 10% of the mass flow rate of the stream for feeding said liquid feedstock, said injection (F2) being located in the top half of the back-washing column (BW),
  said extraction section producing, at the bottom of the washing (W) column, a raffinate comprising at least water, ethanol, acetaldehyde and a portion of said hydrocarbon-based impurity and, at the top of the back-washing (BW) column, an extraction effluent comprising at least a portion of said hydrocarbon-based impurity;
  b) a distillation step comprising:
    at least one acetaldehyde separation step comprising an acetaldehyde separation section, composed of at least one distillation column (D1) fed with the raffinate originating from step a) in an intermediate zone of the column (D1) and producing at the top an acetaldehyde-rich effluent and at the bottom a water/ethanol effluent; and
    at least one ethanol separation step comprising an ethanol separation section, composed of at least one distillation column (D2) fed with the water/ethanol effluent originating from the bottom of the column (D1) in an intermediate zone of the column (D2), and producing at the top an ethanol-rich effluent and at the bottom a water-rich effluent,
    at least one side withdrawal on the column (D1) or the column (D2) of a cut comprising at least one of the compounds ethanol or acetaldehyde, at a mass fraction of at least 10% of the total mass of the withdrawn cut, and said hydrocarbon-based impurity, at a mass fraction of between 0.5% and 50% of the total mass of the withdrawn cut, the side withdrawal being located in an intermediate zone of the column (D1) or (D2).

Preferably, the treatment process according to the invention consists of the liquid-liquid extraction step a) and of the distillation step b), mentioned previously. Even more preferably, the treatment process according to the invention consists of the liquid-liquid extraction step a) and of the distillation step b), the latter consisting of the acetaldehyde separation step comprising the acetaldehyde separation section composed at least of the column (D1), of the ethanol separation step comprising the ethanol separation section composed at least of the column (D2), and of the side withdrawal.

The Feedstock

The process according to the invention applies to the treatment of liquid feedstocks comprising at least ethanol, water and acetaldehyde and comprising at least one partially polar hydrocarbon-based impurity. It advantageously applies to the treatment of the aqueous-alcoholic effluents from the process for converting ethanol into butadiene, i.e. the Lebedev process.

The liquid feedstock treated by means of the process according to the invention is preferably a solution, suspension or emulsion.

The liquid feedstock to be treated may comprise one or more partially polar hydrocarbon-based impurities, preferably in a small amount, in particular relative to the "noble" compounds (or compounds of industrial interest), i.e. ethanol and acetaldehyde, and relative to the water. The hydrocarbon-based impurity under consideration, i.e. the partially polar hydrocarbon-based impurity to be extracted, or each of the hydrocarbon-based impurities under consideration, notably represents less than 5% by weight, in particular less than 2% by weight, more particularly less than 1% by weight of the liquid feedstock to be treated.

Advantageously, the hydrocarbon-based impurity under consideration has a boiling point between those of the major compounds of the treated feedstock (ethanol, water, acetaldehyde), i.e. between 20° C. and 100° C. at atmospheric pressure. The hydrocarbon-based impurity under consideration may generate, with at least one of the compounds of the liquid feedstock, notably with the water, the ethanol and/or the acetaldehyde, in particular with the water, and/or with the organic extraction solvent from step a) of the process according to the invention and/or the aqueous back-washing solvent from step a) of the process according to the invention, an azeotrope whose boiling point at atmospheric pressure is within this same temperature range, i.e. between 20° C. and 100° C. In this case of forming an azeotrope, with at least one of the compounds of the liquid feedstock and/or with the organic extraction solvent and/or the aqueous back-washing solvent, it is the boiling point of the azeotrope which is considered as limiting and which is thus taken into account.

According to the invention, the hydrocarbon-based impurity under consideration also has partition coefficient values of between 0.1 and 5 at any point in the back-washing (BW) column of the extraction section, preferably between 0.1 and 3 and preferentially between 0.2 and 2. It thus has low affinity with the organic extraction phase comprising the organic extraction solvent but higher affinity than those of ethanol and acetaldehyde (less than or equal to 0.05) with this same organic extraction phase. The hydrocarbon-based impurities, the partition coefficient of which at any point in the back-washing (BW) column of the extraction section is greater than 5, are extracted by simple washing with the organic extraction solvent; the process according to the invention which includes a system for withdrawing and recycling a distillation cut into the washing/back-washing section is not necessary for extracting these impurities with a high partition coefficient (>5).

The hydrocarbon-based impurity or impurities, which it is desired to extract by means of the process according to the invention, are, for example, butanol, ethyl acetate, or any other hydrocarbon-based impurity co-produced during the conversion of ethanol into butadiene and having a boiling point of between 20° C. and 100° C. at atmospheric pressure, or which generate, with at least one of the compounds of the liquid feedstock and/or with the organic extraction solvent and/or with the aqueous back-washing solvent, an azeotrope whose boiling point is between 20 and 100° C. at atmospheric pressure, and a partition coefficient of between 0.1 and 5 at any point in the back-washing (BW) column of the extraction section.

The Extraction Step a)

In accordance with the invention, the treatment process comprises a liquid-liquid extraction step comprising an extraction section with at least one washing (W) column and one back-washing (BW) column. The extraction section produces, at the bottom of the washing (W) column, a raffinate comprising at least water, ethanol, acetaldehyde and a portion of the hydrocarbon-based impurity under consideration and, at the top of the back-washing (BW) column, an extraction effluent comprising at least a portion of the hydrocarbon-based impurity under consideration.

The washing (W) column is fed at the top with the stream originating from the bottom of the back-washing (BW) column and at the bottom with a stream of organic extraction solvent; the back-washing (BW) column is, itself, fed at the top with a stream of aqueous back-washing solvent and at the bottom with the stream originating from the top of the washing (W) column.

According to the invention, the extraction section is fed with the liquid feedstock (F1) to be treated at an intermediate point located between the top of the washing (W) column and the bottom of the back-washing (BW) column. Preferably, the liquid feedstock (F1) to be treated feeds the extraction section upstream of the top of the washing (W) column, to undergo, first, counter-current washing with the organic extraction solvent.

Thus, in an entirely conventional manner, the feedstock to be treated according to the invention is washed counter-currentwise with the organic extraction solvent in the washing (W) column. The apolar or sparingly polar impurities (impurities with a partition coefficient of greater than 5 at any point in the back-washing (BW) column of the extraction section) are extracted into the washing solvent. The organic stream is then washed counter-currentwise with the aqueous solvent, thus making it possible to back-extract from the organic solvent the "noble" compounds (i.e. the compounds of interest), ethanol and acetaldehyde, which may be dissolved in the organic solvent. This washing/back-washing principle makes it possible to minimize the losses of ethanol and acetaldehyde during this step.

In accordance with the invention, the extraction section comprises at least one injection (F2) of the cut(s) withdrawn in step b) of the process according to the invention. Advantageously, the injection(s) (F2) are located in the top half of the back-washing (BW) column, preferably in the top part of the back-washing (BW) column such that the distance between the top of the back-washing (BW) column and the injection (F2) is equal to a length of between 10% and 30% of the total length of the back-washing (BW) column, the 0% position meaning that the injection F2 is located at the top of the back-washing (BW) column and the 100% position meaning that the injection F2 is located at the bottom of the back-washing (BW) column.

Advantageously, the withdrawn and recycled stream (F2), or each withdrawn and recycled stream (F2), is injected at a mass flow rate of between 0.1% and 10% of the mass flow rate of the liquid feedstock feeding the extraction section according to the invention. The withdrawn and recycled stream (F2) comprises the hydrocarbon-based impurity under consideration at a mass concentration advantageously between 0.5% and 50%, preferably between 1% and 30%, relative to the mass of the recycled stream (F2).

Recycling of the cut withdrawn in step b) of the process according to the invention, notably into a precise injection point (F2) on the back-washing (BW) column allows the at least partial extraction of the hydrocarbon-based impurity under consideration, for example butanol, with a satisfactory extraction efficiency, notably greater than 10% by weight, in particular between 15% and 35% by weight, for example of the order of 20% to 30% by weight, for ethanol losses of less than 0.1% by weight, advantageously less than or equal to 0.05% by weight, and acetaldehyde losses of less than 0.1% by weight, advantageously less than or equal to 0.05% by weight, these judged losses being considered as low or even negligible.

According to the invention, the extraction efficiency corresponds to the ratio between the mass amount of hydrocarbon-based impurity under consideration extracted into the extraction effluent leaving at the top of the back-washing (BW) column, and the mass amount of said hydrocarbon-based impurity entering the extraction section (i.e. present in the feedstock to be treated). The loss of ethanol corresponds to the ratio between the mass amount of ethanol extracted into the extraction effluent leaving the top of the back-washing (BW) column and the mass amount of ethanol entering the extraction section (i.e. present in the feedstock to be treated).

Partial extraction of the hydrocarbon-based impurity under consideration, for example butanol, is sufficient to stabilize its content in the recycling loop and to purge all of the hydrocarbon-based impurity under consideration produced in the reaction sections of the process for converting ethanol into butadiene, and this being for a reasonable cost.

According to the invention, the mass flow rate of organic extraction solvent (the washing solvent) is advantageously between 25% and 200%, preferably between 30% and 150%, of the mass flow rate of the liquid feedstock feeding the extraction section according to the invention. The mass flow rate of aqueous back-washing solvent is advantageously between 10% and 80%, preferably between 10% and 50%, of the mass flow rate of the liquid feedstock feeding the extraction section according to the invention.

The criteria for selecting the organic extraction solvent are well known to those skilled in the art, for instance the affinity for the impurities to be extracted, the physical properties of the organic solvent such as the density, which must be sufficiently different from that of the back-washing solvent, the viscosity, which must not be too high (preferably less than or equal to 5 cPs at room temperature), a boiling point which is sufficiently remote from those of the impurities to be extracted, the cost of the organic solvent, etc. In the particular case of the liquid feedstock to be treated, obtained from the process for producing butadiene from ethanol (Lebedev process), a person skilled in the art knows how to select the organic extraction solvent that is the most suitable notably as a function of the apolar or sparingly polar impurities contained in the feedstock to be treated, for instance diethyl ether. Preferably, the organic extraction solvent is chosen from saturated and/or unsaturated and/or aromatic hydrocarbons. The organic extraction solvent is advantageously a hydrocarbon or a mixture of hydrocarbons containing between 6 and 40 carbon atoms, preferably between 10 and 20 carbon atoms, for instance hexadecane. It may also be a desulfurized gas oil or kerosene cut or alternatively a hydrocarbon cut produced by a unit of Fischer-Tropsch type.

According to the invention, the aqueous back-washing solvent is a neutral, acidic or basic aqueous solvent. Preferably, the aqueous solvent used for the back-washing in the process is water or acidified water with a pH of between 0.5 and 5.

In one particular embodiment of the invention, the washing column comprises between 2 and 10 theoretical stages, preferably between 3 and 7 theoretical stages and notably 5 theoretical stages, and the back-washing column comprises between 1 and 6 theoretical stages, preferably between 2 and 4 theoretical stages.

Advantageously, the liquid-liquid extraction step is performed, in each of the washing and back-washing columns, at a temperature of between 10° C. and 70° C., preferably between 20° C. and 55° C., and at a pressure of between 0.1 MPa and 0.5 MPa. The residence times are typically between 0.5 and 10 hours, preferably between 0.5 and 6 hours, in the washing column and between 0.5 and 6 hours, preferably between 1 and 3 hours, in the back-washing column.

Advantageously, the organic extraction solvent may then be recovered at the outlet of the extraction section and then regenerated, for example by distillation, to be reused in the washing column.

Distillation Step b)

In accordance with the invention, the treatment process comprises a distillation step comprising at least one acetaldehyde separation step comprising an acetaldehyde separation section and at least one ethanol separation step comprising an ethanol separation section.

The acetaldehyde separation section comprises at least one distillation column (D1). The column (D1) is fed in an intermediate zone with raffinate obtained from step a), more precisely obtained from the bottom of the washing (W) column of step a), said raffinate comprising at least water, ethanol, acetaldehyde and hydrocarbon-based impurity under consideration. The acetaldehyde separation section produces, at the top of column (D1), an acetaldehyde-rich effluent, and, at the bottom of column (D1), a water/ethanol effluent.

The acetaldehyde-rich effluent produced at the top of column (D1) comprises at least 50% by weight, preferably at least 70% by weight and preferentially 80% by weight of acetaldehyde. It may thus be recycled into the reaction section for producing butadiene where the acetaldehyde may be used as reagent.

The water/ethanol effluent produced at the bottom of column (D1) may comprise the hydrocarbon-based impurity under consideration, for example butanol.

The ethanol separation section comprises at least one distillation column (D2). Column (D2) is fed with water/ethanol effluent obtained from the bottom of column (D1) in an intermediate zone. The ethanol separation section produces, at the top of column (D2), an ethanol-rich effluent and, at the bottom of column (D2), a water-rich effluent.

The ethanol-rich effluent produced at the top of column (D2) comprises at least 70% by weight and preferably at least 80% by weight of ethanol. It also comprises water. The ethanol-rich effluent may thus be recycled into the reaction section in which the ethanol will be consumed as reagent.

The water-rich effluent essentially comprises water. In particular, the water-rich effluent comprises water and less than 10 ppm by mass, preferably less than 5 ppm by mass, of ethanol, less than 5 ppm by mass of acetaldehyde, and less than 5 ppm by mass, preferably less than 1 ppm, of partially polar hydrocarbon-based impurity.

According to the invention, the distillation step comprises at least one side withdrawal on column (D1) or (D2). The withdrawn cut is then recycled into the back-washing (BW) column of step a).

The side withdrawal is located in a zone at an intermediate height on one or other of the columns (D1) and (D2). The choice of column (D1) or (D2) for the side withdrawal depends on the hydrocarbon-based impurity that it is desired to extract. For example, when the hydrocarbon-based impurity to be extracted is butanol, the side withdrawal takes place in an intermediate zone on column (D2).

Advantageously, the withdrawn stream comprises at least one of the compounds of interest of the feedstock (ethanol, acetaldehyde), in a mass content at least equal to 10%, preferably at least equal to 20%. Thus, when the withdrawn stream comprises only one of the two compounds, ethanol or acetaldehyde, the mass content of this compound of interest in the withdrawn stream is at least equal to 10%, preferably at least equal to 20%. When the withdrawn stream comprises both compounds of interest, ethanol and acetaldehyde, the sum of the mass contents of ethanol and acetaldehyde is at least equal to 10%, preferably at least equal to 20%. The withdrawn stream may also comprise water.

Advantageously, the withdrawn stream comprises the partially polar hydrocarbon-based impurity under consideration. The mass fraction of said hydrocarbon-based impurity in the withdrawn stream is advantageously between 0.5% and 50%, preferably between 1% and 30%.

The withdrawn stream may be a one-phase or two-phase stream.

Advantageously, the acetaldehyde separation section and/or the ethanol separation section may also comprise a reflux system at the top of the distillation column (D1) and/or (D2) for ensuring reflux of the distillate and a reboiling system at the bottom of column (D1) and/or (D2). The reflux and reboiling systems which may be used at the top and bottom of column is (D1) and (D2) are those that are well known to a person skilled in the art.

The examples that follow are presented as nonlimiting illustrations of the treatment process according to the invention.

EXAMPLES

Example 1—Extraction of Butanol According to the Process of the Invention

Figure 1:
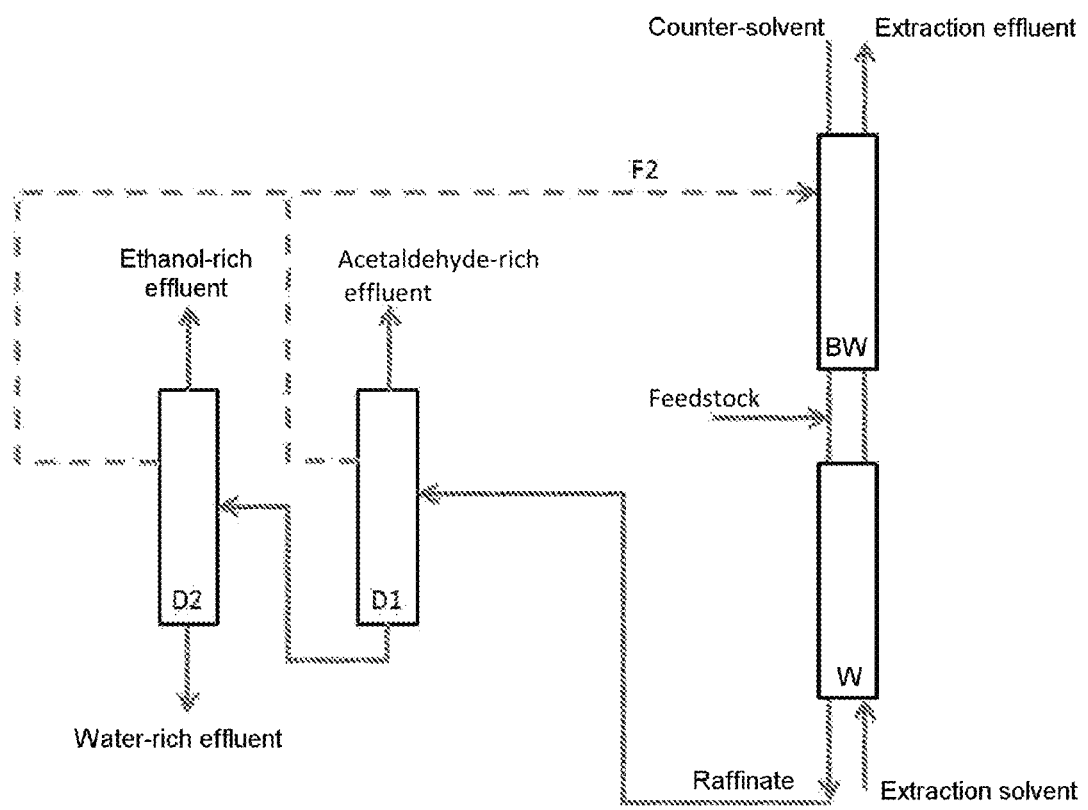
FIG. 1: Scheme of the process according to the invention, the distillation section of step b) comprising a side withdrawal on column (D1) and/or a side withdrawal on column (D2).
Figure 2:
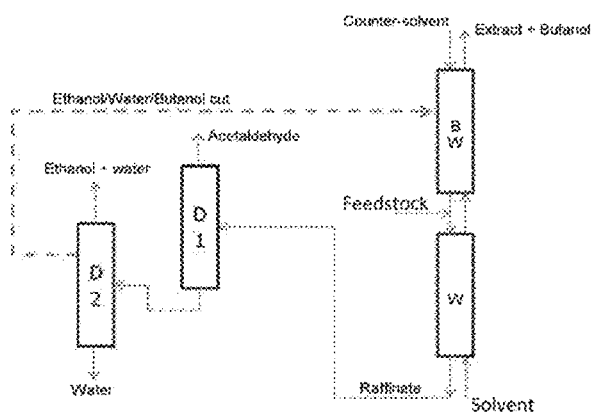
FIG. 2: Scheme of the process according to the invention in the case where the hydrocarbon-based impurity to be extracted is butanol, as in Example 1.
Figure 3:
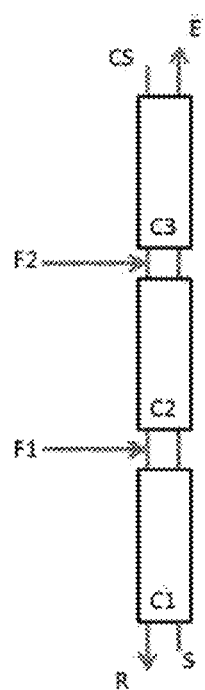
FIG. 3: Scheme of the cutting of the extraction section in Example 1, C1 being the washing (W) column, the zones C2 and C3 being the lower and upper zones, respectively, of the back-washing (BW) column, below and above the injection of the recycled withdrawn stream F2, F1 being the stream of the liquid feedstock to be treated, S the stream of organic extraction solvent, CS the stream of aqueous back-washing solvent and the extraction effluent (E) leaving at the top of the back-washing column in which the hydrocarbon-based impurity under consideration is extracted, and the raffinate (R) leaving at the bottom of the washing column and which will then be directed toward the distillation section.

The calculation of the butanol extraction performance is made using the Kremser analytical solutions and by dividing the back-washing (BW) column into two zones (C2 and C3). The calculations were made by varying the position of the injection F2, i.e. the ratio of the heights C3/(C2+C3), C3 being the height of the upper zone of the back-washing (BW) column above the injection F2 and C2 the height of the lower zone of the back-washing (BW) column below the injection F2. FIG. 3 schematically represents the cutting of the extraction section: C1 being the washing (BW) column and zones C2 and C3 being the lower and upper zones, respectively, of the back-washing (BW) column. The calculations are made based on the hypothesis of constant partition coefficients in each zone.

The operating conditions used:
number of theoretical stages in the washing (W) column: 5
number of theoretical stages in the back-washing (BW) column: 2 or 4
organic extraction solvent (washing solvent) (S): hexadecane
aqueous back-washing solvent (BS): water
flow rates by volume Qv and by mass Qm and mass composition of the streams F1 (the liquid feedstock to be treated), F2 (the recycled withdrawal), S (the organic extraction solvent) and BS (the aqueous back-washing solvent): (cf. Table 1)

TABLE 1 flow rates by volume Qv and by mass Qm and mass composition of the streams F1, F2, S and BS

|  | F1 | F2 | S | BS |
|---|---|---|---|---|
| Qv (l/h) | 1 | 0.031579 | 0.8 | 0.2 |
| Qm (kg/h) | 0.875 | 0.027632 | 0.6288 | 0.198 |
| Mass flow rate relative to F1 (weight %) | 1 | 3.2% | 72% | 23% |
| Composition (weight %): |  |  |  |  |
| Ethanol | 65.9% | 43% | 0 | 0 |
| Acetaldehyde | 5% | 0 | 0 | 0 |
| Diethyl ether | 1% | 0 | 0 | 0 |
| Butanol | 0.5% | 9% | 0 | 0 |
| Water | 27% | 48% | 0 | 97% |
| Hexadecane | 0% | 0 | 100% | 0 |
| Acetic acid | 0.6% | 0 | 0 | 3% |

Partition coefficients (M) of the compounds of the feedstock F1 in zone C2 of the back-washing (BW) column: (cf. Table 2).

TABLE 2

Partition coefficients in zone C2 of the back-washing column:

|  | M |
|---|---|
| Ethanol | 0.014 |
| Acetaldehyde | 0.03 |
| Diethyl ether | 3.4 |
| Butanol | 0.3 |
| Water | — |

The amount of butanol extracted, i.e. recovered in the extraction effluent (E) at the top of the back-washing column, relative to the mass amount of butanol entering the extraction section via the stream F1, is calculated for different positions of the injection F2 on the back-washing (BW) column, i.e. for different ratios C3/(C2+C3), and for the two dimensionings of the back-washing column (2 or 4 theoretical stages), the 0% position meaning that the injection F2 is at the top of the back-washing (BW) column and the 100% position meaning that the injection F2 is at the bottom of the back-washing (BW) column. Simultaneously, the ethanol losses, i.e. the mass amount of ethanol extracted into the extraction effluent (E) relative to the mass amount of ethanol entering the extraction section via the stream F1, are also calculated for the different positions of the injection F2, the ethanol extracted into the extraction effluent (E) which cannot be recycled into the process for converting ethanol into butadiene being considered as lost. The results are shown in FIG. 4.

Figure 4:
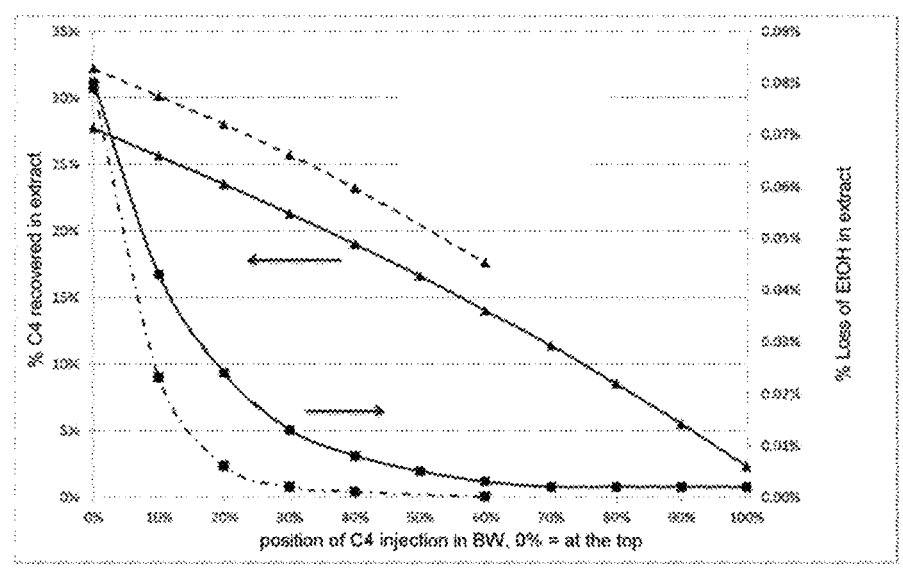
FIG. 4: Butanol extraction efficiency (▲) and loss of ethanol (■) as a function of the position of injection F2, the 0% position representing an injection at the top of the back-washing (BW) column, and for the two dimensionings of the back-washing (BW) column, 2 (solid lines) or 4 (dotted lines) theoretical stages, in the process of Example 1.

From FIG. 4, it is seen that a position of injection F2 (ratio C3/(C2+C3)) on the back-washing column of between 10% and 30% makes it possible to obtain a butanol extraction with an efficiency of the order of 20% to 30% by weight, for a negligible ethanol loss (less than 0.03% by weight).

Example 2—Extraction of Various Hydrocarbon-Based Impurities

The same calculations as in Example 1 are made for various hydrocarbon-based impurities to be extracted: methanol, butanol, ethyl acetate. The calculations are made with the same starting hypotheses, the same mass flow rates of the streams as those of Example 1 and equivalent compositions (9% by weight of the hydrocarbon-based impurity under consideration in the feedstock to be treated).

The other operating conditions used are:
number of theoretical stages in the washing (W) column: 5
number of theoretical stages in the back-washing (BW) column: 2
organic extraction solvent (washing solvent) (S): hexadecane
aqueous back-washing solvent (BS): water
position of the injection F2 (C3/(C2+C3)) on the column (BS): 20%

Table 3 collates the boiling points of the hydrocarbon-based impurities under consideration (methanol, butanol, ethyl acetate), or of their azeotrope formed with water, and their partition coefficients (M) in zone C2 of the back-washing (BW) column.

The extraction efficiencies obtained for each of the impurities methanol, butanol and ethyl acetate are presented in Table 3.

TABLE 3

Boiling points (b.p.) (or azeotropes formed with water) and partition coefficients (M) of the hydrocarbon-based impurities under consideration and calculated extraction efficiencies

| Species | b.p. (° C.) | Partition coefficient (M) | Extraction efficiency (extracted weight %) |
|---|---|---|---|
| Methanol | 65 | 0.005 | 0.02% |
| Butanol | 93° C.* | 0.3 | 24% |
| Ethyl acetate | 70** | 2.4 | 96% |

*n-Butanol/water azeotrope
**Ethyl acetate/water azeotrope

The extraction efficiency is very high (96%) in the case of ethyl acetate, the partition coefficient of which in zone C2 of the back-washing (BW) column is 2.4.

For butanol, the extraction efficiency equal to 24% under the operating conditions used is very satisfactory. Butanol is thus partially extracted, as expected.

Conversely, methanol, the partition coefficient of which is very low (equal to 0.005, very much less than 0.1) is very sparingly or not at all extracted (0.02% by weight extracted).

Example 3—Process for Treating the Feedstock in the Withdrawal-Recycling System (not in Accordance)

The same feedstock as that of Example 1 is treated in a process comprising a liquid-liquid extraction section, with washing (W) and back-washing (BW) columns and hexadecane as extraction solvent, and a distillation section comprising two distillation columns (D1) and (D2). The same washing (W), back-washing (BW) and distillation (D1) and (D2) columns as those of Example 1 are used. The process used in this Example 3 does not comprise any withdrawal in the distillation section; there is thus no injection (F2) into the back-washing column.

The other operating conditions (flow rate and composition of the feedstock F1, flow rates and compositions of the solvent and counter-solvent, partition coefficients) are also the same as those of Example 1.

Under these conditions, the degree of extraction of butanol is 1.8% (instead of 20% to 30% according to Example 1).

The butanol not extracted which then accumulates in column (D2) is mainly extracted with the ethanol effluent at the top of column (D2).

The invention claimed is:

1. A process for the treatment by liquid-liquid extraction and distillation of a liquid feedstock comprising at least ethanol, water and acetaldehyde and at least one hydrocarbon-based impurity with a boiling point of between 20° C. and 100° C. at atmospheric pressure, or generating, with at least one of the compounds of the liquid feedstock and/or with the organic extraction solvent and/or with the aqueous back-washing solvent, an azeotrope whose boiling point is between 20 and 100° C. at atmospheric pressure, and a partition coefficient of between 0.1 and 5 at any point in the back-washing (BW) column of the extraction section, comprising:

a) a liquid-liquid extraction step comprising an extraction section comprising a washing (W) column and a back-washing (BW) column, said extraction section being fed with said liquid feedstock at an intermediate point located between the top of the washing (W) column and the bottom of the back-washing (BW) column, said washing (W) column being fed at the top with the stream originating from the bottom of the back-washing (BW) column and at the bottom with a stream of an organic extraction solvent, said back-washing (BW) column being fed at the top with a stream of an aqueous back-washing solvent and at the bottom with the stream originating from the top of the washing (W) column, said extraction section comprising at least one injection (F2) of the cut withdrawn in step b), said injection (F2) being located in the top half of the back-washing (BW) column, said extraction section producing, at the bottom of the washing (W) column, a raffinate comprising at least water, ethanol, acetaldehyde and a portion of said hydrocarbon-based impurity and, at the top of the back-washing (BW) column, an extraction effluent comprising at least a portion of said hydrocarbon-based impurity;

b) a distillation step comprising:

at least one acetaldehyde separation step comprising an acetaldehyde separation section, composed of at least one distillation column (D1) fed with the raffinate originating from step a) in an intermediate zone of the column (D1) and producing at the top an acetaldehyde-rich effluent and at the bottom a water/ethanol effluent; and at least one ethanol separation step comprising an ethanol separation section, composed of at least one distillation column (D2) fed with the water/ethanol effluent originating from the bottom of the column (D1) in an intermediate zone of the column (D2), and producing at the top an ethanol-rich effluent and at the bottom a water-rich effluent, at least one side withdrawal on the column (D1) or the column (D2) of a cut comprising at least one of the compounds ethanol or acetaldehyde, at a mass fraction of at least 10% of the total mass of the withdrawn cut, and said hydrocarbon-based impurity, at a mass fraction of between 0.5% and 50% of the total mass of the withdrawn cut, the side withdrawal being located in an intermediate zone of the column (D1) or (D2).

2. The treatment process as claimed in claim 1, in which the feedstock comprises less than 5% by weight of hydrocarbon-based impurity.

3. The treatment process as claimed in claim 1, in which the hydrocarbon-based impurity has a partition coefficient of between 0.2 and 2 at any point in the back-washing (BW) column of the extraction section.

4. The treatment process as claimed in claim 1, in which the injection (F2) is located in the top part of the back-washing (BW) column such that the distance between the top of the back-washing (BW) column and the injection (F2) is equal to a length of between 10% and 30% of the total length of the back-washing (BW) column.

5. The treatment process as claimed in claim 1, in which the recycled stream (F2) is injected into step a) at a mass flow rate of between 0.1% and 10% of the mass flow rate of the liquid feedstock feeding the extraction section.

6. The treatment process as claimed in claim 1, in which the recycled stream (F2) comprises the hydrocarbon-based impurity at a mass concentration of between 0.5% and 50%.

7. The treatment process as claimed in claim 1, in which the mass flow rate of organic extraction solvent in step a) is between 25% and 200% of the mass flow rate of the liquid feedstock feeding the extraction section.

8. The treatment process as claimed in claim 1, in which the mass flow rate of aqueous solvent in step a) is between 10% and 80% of the mass flow rate of the liquid feedstock feeding the extraction section.

9. The treatment process as claimed in claim 1, in which the liquid-liquid extraction step is performed at a temperature of between 10° C. and 70° C., at a pressure of between 0.1 MPa and 0.5 MPa and with residence times of between 0.5 and 10 hours in the washing column and between 0.5 and 6 hours in the back-washing column.

* * * * *